(12) United States Patent
Maekawa et al.

(10) Patent No.: US 11,813,440 B2
(45) Date of Patent: Nov. 14, 2023

(54) INTRADERMAL NEEDLE, PACKAGED ARTICLE, AND INJECTION DEVICE

(71) Applicant: TERUMO KABUSHIKI KAISHA, Tokyo (JP)

(72) Inventors: Minami Maekawa, Kanagawa (JP); Yoichiro Iwase, Kanagawa (JP); Eiji Kawamoto, Kanagawa (JP); Kentaro Nakajima, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/815,794

(22) Filed: Mar. 11, 2020

(65) Prior Publication Data

US 2020/0206434 A1    Jul. 2, 2020

Related U.S. Application Data

(63) Continuation of application No. PCT/JP2019/007241, filed on Feb. 26, 2019.

(30) Foreign Application Priority Data

Mar. 12, 2018  (JP) ................................ 2018-043852

(51) Int. Cl.
*A61M 5/46*     (2006.01)
*A61M 5/32*     (2006.01)
(Continued)

(52) U.S. Cl.
CPC .......... *A61M 5/3243* (2013.01); *A61M 5/002* (2013.01); *A61M 5/3286* (2013.01);
(Continued)

(58) Field of Classification Search
CPC ...... A61M 5/3293; A61M 5/46; A61M 5/425; A61M 5/42; A61M 5/422; A61M 5/427
See application file for complete search history.

(56) References Cited

U.S. PATENT DOCUMENTS

2012/0191042 A1    7/2012  Iwase et al.
2018/0133410 A1 *  5/2018  Ura ........................ A61M 5/425
(Continued)

FOREIGN PATENT DOCUMENTS

EP          3 275 490 A1       1/2018
JP    WO 2012132761 A1 *  10/2012   .............. A61M 5/46
(Continued)

OTHER PUBLICATIONS

International Search Report (PCT/ISA/210) dated Mar. 26, 2019, by the Japanese Patent Office as the International Searching Authority for International Application No. PCT/JP2019/007241.
(Continued)

*Primary Examiner* — Emily L Schmidt
(74) *Attorney, Agent, or Firm* — BUCHANAN INGERSOLL & ROONEY PC (57) ABSTRACT

There are provided an intradermal needle, a packaged article, and an injection device. The intradermal needle includes: a tubular needle that has a needle tip capable of puncturing a living body; a needle hub that holds the tubular needle; a flange part that extends in a flange shape from the needle hub; and a ring projection that extends toward a leading end of the flange part and is formed in a cylindrical shape to surround the tubular needle. The flange part has a cut portion formed by partially cutting to achieve downsizing of the flange part.

20 Claims, 9 Drawing Sheets

(51) Int. Cl.
 *A61M 5/00* (2006.01)
 *A61M 5/42* (2006.01)
(52) U.S. Cl.
 CPC .......... *A61M 5/3293* (2013.01); *A61M 5/425* (2013.01); *A61M 5/46* (2013.01)

(56) References Cited

U.S. PATENT DOCUMENTS

| 2020/0206432 A1 | 7/2020 | Nakajima et al. |
| 2020/0206433 A1 | 7/2020 | Nakajima et al. |

FOREIGN PATENT DOCUMENTS

| JP | 5366195 B2 | 12/2013 | |
| JP | 5366196 B2 | 12/2013 | |
| JP | WO 2014033898 A1 * | 3/2014 | .......... A61M 5/3293 |
| JP | 2015066105 A | 4/2015 | |
| JP | WO 2016117164 A1 * | 7/2016 | .......... A61M 5/3293 |
| WO | 2006/007629 A1 | 1/2006 | |
| WO | WO 2006007629 A1 * | 1/2006 | ............ A61M 5/425 |
| WO | 2011040188 A1 | 4/2011 | |
| WO | 2014033898 A1 | 3/2014 | |
| WO | WO-2017010564 A1 * | 1/2017 | .......... A61M 5/3286 |

OTHER PUBLICATIONS

Written Opinion (PCT/ISA/237) dated Mar. 26, 2019, by the Japanese Patent Office as the International Searching Authority for International Application No. PCT/JP2019/007241.

The extended European Search Report dated May 18, 2020, by the European Patent Office in corresponding European Patent Application No. 19768450.9-1122. (8 pages).

* cited by examiner

| | $D_{mm}$ | $d_{mm}$ | $W_{1mm}$ | $W_{2mm}$ | $W_{3mm}$ |
|---|---|---|---|---|---|
| COMPARATIVE EXAMPLE | 13.09 (=13.1) | 12.0 | 19.1 | 19.1 | |
| 10A | 13.09 (=13.1) | 12.0 | 19.1 | 10.0 | |
| 10B | 13.09 (=13.1) | 12.0 | 19.1 | 16.1 | |
| 10C | 13.09 (=13.1) | 12.0 | 19.1 | 13.1 | 15.0 |

DIAMETER OF NEEDLE TUBE 33G

INTRADERMAL NEEDLE, PACKAGED ARTICLE, AND INJECTION DEVICE

CROSS-REFERENCES TO RELATED APPLICATIONS

This application is a continuation of International Application No. PCT/JP2019/007241 filed on Feb. 26, 2019, which claims priority to Japanese Application No. 2018-043852 filed on Mar. 12, 2018, the entire content of both of which is incorporated herein by reference.

FIELD OF THE INVENTION

The present invention generally relates to an intradermal needle used for injecting a drug into a living body, a packaged article that includes an intradermal needle, and an injection device.

BACKGROUND DISCUSSION

Conventionally, an intradermal needle has been proposed for injecting a drug into an upper layer of the skin as disclosed in Japanese Patent No. 5366195 and Japanese Patent No. 5366196. The intradermal needle is intended to puncture the upper layer of the skin with a needle tube protruding a relatively small amount beyond the leading end of a needle hub at an appropriate depth, and is required to have a constant puncture depth.

Therefore, the intradermal needle is provided with a wall-shaped ring projection surrounding the needle tube. The ring projection is pressed against the skin surface by a predetermined pressing force to push out the skin around the needle tube and adjust the skin surface perpendicular to the needle tube, thereby playing the role of keeping constant the puncture depth of the needle tip.

Further, the intradermal needle is provided with a flange part to notify a user of an appropriate pressing force of the ring projection. The flange part is a part that extends in a flange shape on the outer peripheral side of the needle hub. The contact of the flange part with the skin surface makes it possible to inform the user that the ring projection is pressed into the skin by an appropriate pressing force.

SUMMARY

However, the conventional intradermal needle has a large flange part, so it is difficult to provide a safety mechanism such as a protector to prevent erroneous puncture after use. In addition, the conventional intradermal needle is hard to use for a narrow part such as a child's arm.

Disclosed here is an intradermal needle, a packaged article that includes an intradermal needle, and an injection device which are easy to provide a safety mechanism and are suitable for use in a narrow part, and have the same performance as conventional ones.

An intradermal needle according to one aspect includes: a tubular needle that includes a needle tip configured to puncture a living body, a needle hub that holds the tubular needle and possesses a leading end configured to be brought into contact with a living body and a base end configured to receive a syringe, and a flange part that extends radially outwardly from the needle hub and that possesses a leading end side facing towards the leading end of the needle hub. An annular projection extends axially away from the leading end side of the flange part toward the leading end of the needle hub, and the annular projection possesses a cylindrical shape and surrounds a leading end portion of the tubular needle. The flange part includes a cut portion along at least one portion of the flange part so that a width dimension of the flange part at the cut portion is less than the width dimension of the flange part at a part of the flange part other than the cut portion.

According to the above-mentioned intradermal needle, the flange part has the cut portion smaller in width in the predetermined direction than the other portion. Thus, even when the flange part has the cut portion, it is possible to implement the flange part reduced in size that can indicate an appropriate pressing force of the ring projection, facilitate the provision of a safe mechanism such as a protector for preventing erroneous puncturing after use, and allow the use of the intradermal needle for narrow body parts.

In the above-mentioned intradermal needle, the cut portion may be provided in a region on the outer peripheral side of the ring projection. According to this configuration, the cut portion can be provided in the flange part without impairing the function of the ring projection.

In the above-mentioned intradermal needle, the cut portion may have a first chipped portion in which one end of the flange part is cut, and a second chipped portion in which the flange part is cut at a position facing the first chipped portion with the needle hub interposed therebetween. Even in the case of this configuration, the ring projection can be pressed with a constant pressing force by pressing an outer peripheral portion of the flange part, which is not cut, to the extent that it comes into contact with the skin. The flange part can be reduced in size by the first chipped portion and the second chipped portion, which facilitates the provision of a safety mechanism such as a protector for preventing erroneous puncturing after use and makes it easy to use the intradermal needle for narrow body parts.

In the above case, the first chipped portion and the second chipped portion may be formed substantially in parallel. The cut portion may be cut linearly. The flange part may be formed in a disk shape centering on the needle hub at a portion other than the cut portion.

In the above-described intradermal needle, a distance between the first chipped portion and the second chipped portion may be smaller than a diameter of the ring projection. As a result, the flange part can be further reduced in size. Even with this flange part, it is possible to inform the user that the ring projection is pressed with a constant pressing force.

A packaged article according to another aspect includes: a container possessing an open end, a seal member covering the open end of the container so that the container is a sealed container, and an intradermal needle positioned in the sealed container. The intradermal needle comprises a tubular needle that includes a needle tip configured to punctures a living body, a needle hub that holds the tubular needle and possesses a leading end configured to be brought into contact with a living body and a base end configured to receive a syringe, and a flange part that extends radially outwardly from the needle hub and possessing a leading end side facing towards the leading end of the needle hub. An annular projection extends axially away from the leading end side of the flange part toward the leading end of the needle hub, and the annular projection possesses a cylindrical shape and surrounds the leading end portion of the tubular needle. The flange part includes a cut portion along at least one portion of the flange part so that a width dimension of the flange part at the cut portion is less than the width dimension of the flange part at a part of the flange part other than the cut portion.

According to still another aspect, an injection device includes: an intradermal needle and a syringe detachably attached to the intradermal needle. The intradermal needle includes a tubular needle that includes a needle tip configured to punctures a living body, a needle hub that holds the tubular needle and possesses a leading end configured to be brought into contact with a living body and a base end configured to receive a syringe, and a flange part that extends radially outwardly from the needle hub and possessing a leading end side facing towards the leading end of the needle hub. An annular projection extends axially away from the leading end side of the flange part toward the leading end of the needle hub, and the annular projection possesses a cylindrical shape and surrounds the leading end portion of the tubular needle. The flange part includes a cut portion along at least one portion of the flange part so that a width dimension of the flange part at the cut portion is less than the width dimension of the flange part at a part of the flange part other than the cut portion.

According to this configuration, the intradermal needle is reduced in size by the provision of the cut portion, which facilitates the provision of a safety mechanism such as a protector for preventing erroneous puncturing after use and makes it easy to use the injection device for narrow body parts such as a child's arm.

According to the intradermal needle, the packaged article, and the injection device in the above aspects, the flange part is reduced in size by the cut portion, which facilitates the provision of a safety mechanism such as a protector for preventing erroneous puncturing after use and makes it easy to use the intradermal needle, the packaged article, and the injection device for narrower body parts.

DETAILED DESCRIPTION

Set forth below with reference to the accompanying drawings is a detailed description of embodiments of an intradermal needle, a package that includes an intradermal needle, and an injection device representing examples of the inventive intradermal needle, packaged article and injection device disclosed here.

Figure 1:
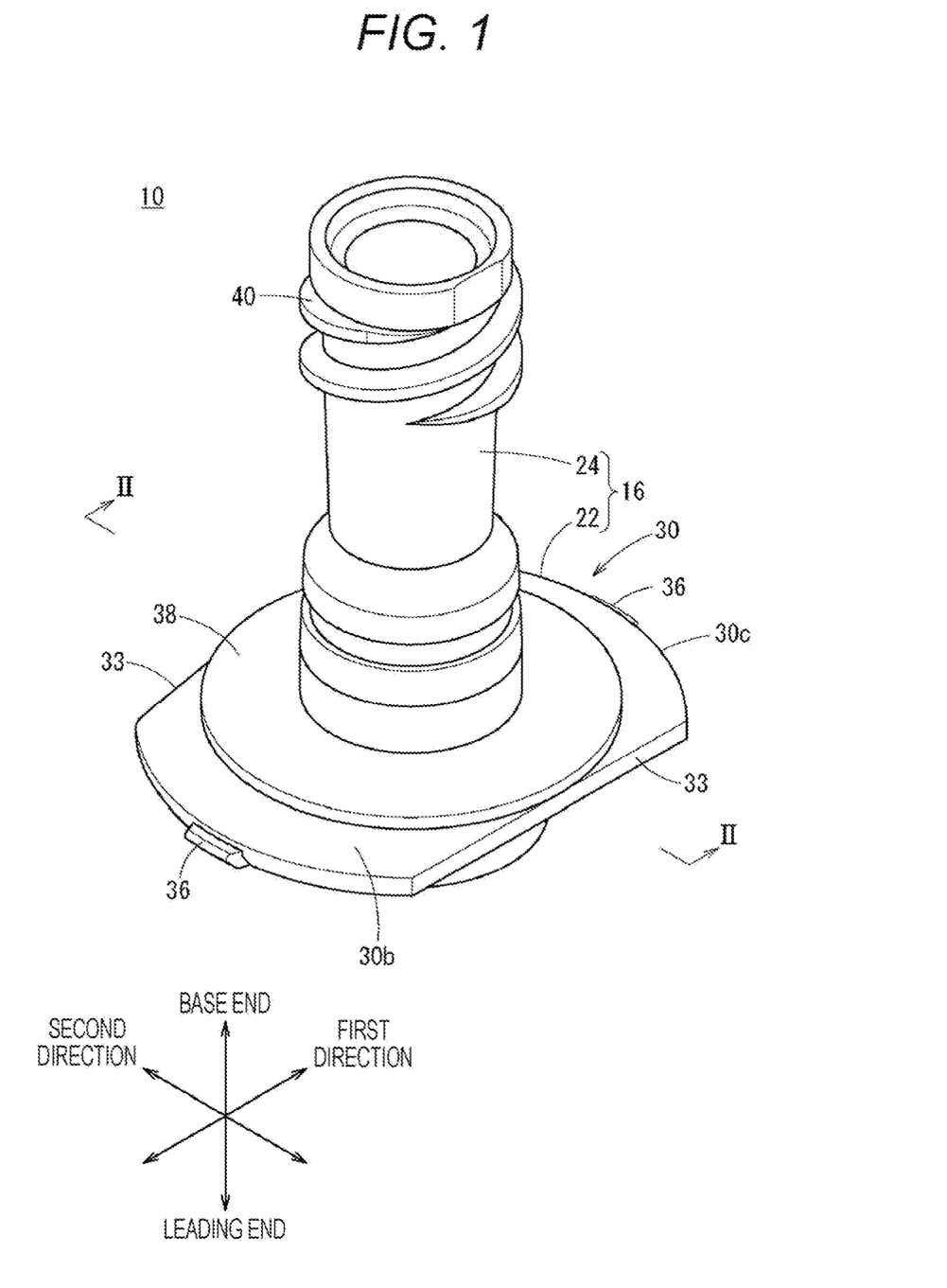
FIG. 1 is a perspective view of an intradermal needle according to an embodiment disclosed here.
Figure 2:
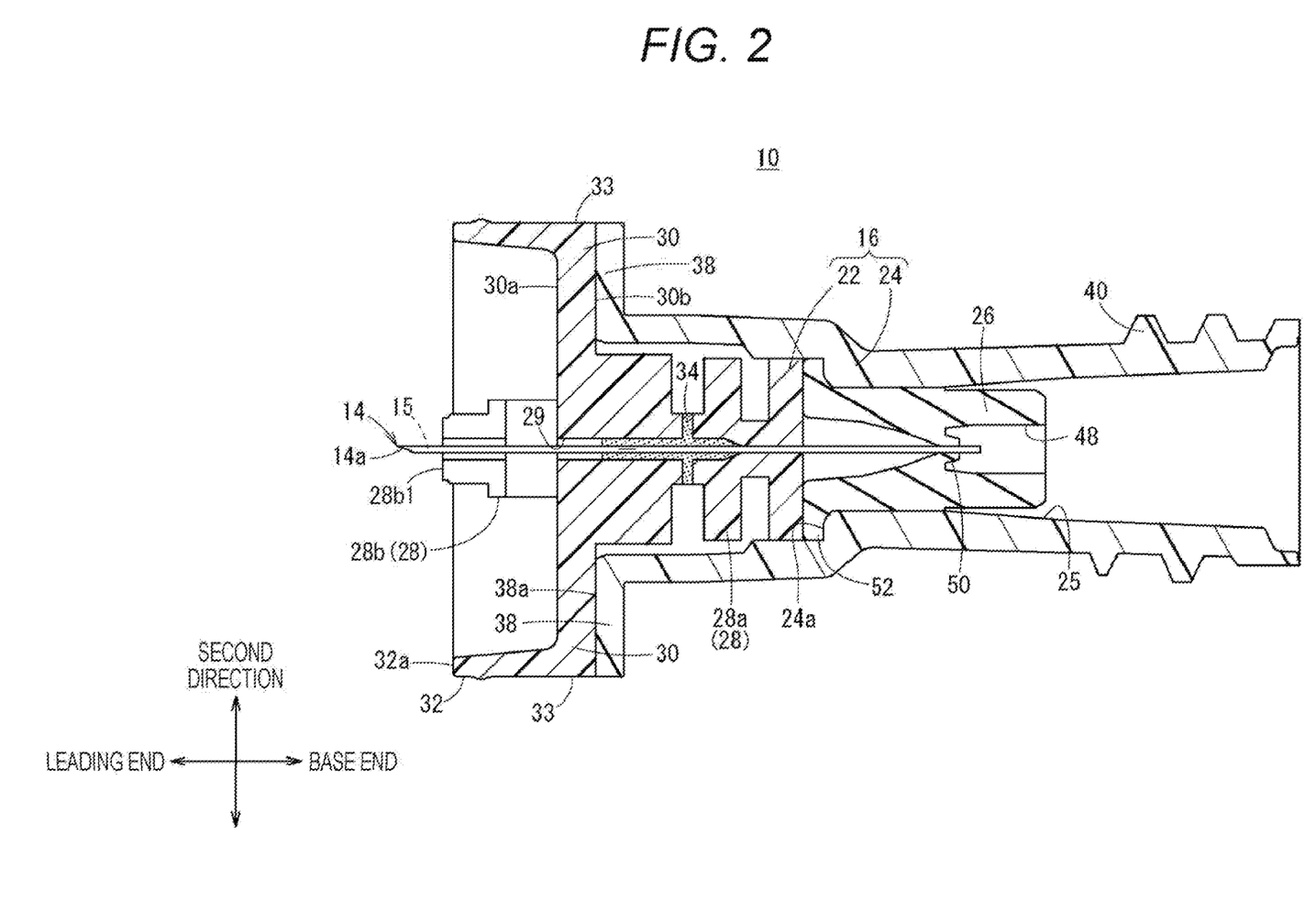
FIG. 2 is a cross-sectional view of FIG. 1 taken along the section line II-II in FIG. 1.

Hereinafter, components of an intradermal needle 10 (medical needle) will be described. As shown in FIG. 1, the intradermal needle 10 includes: a first member 22 that has a flange part 30 provided on a leading end side; and a second member 24 that is provided on a base end side and has a male screw portion 40 for attaching a syringe 20. The first member 22 and the second member 24 constitute a needle hub 16 possessing a substantially cylindrical shape. The needle hub holds a tubular needle 14 inside the needle hub 16 as shown in FIG. 2.

The tubular needle 14 is formed as a rigid hollow tube having a needle lumen or axially extending hole 15 at a center axis of the tubular needle 14. The tubular needle 14 has a needle tip 14*a* with a sharp blade surface at an extreme tip. The diameter of the tubular needle 14 is not particularly limited, but is, for example, a size of 26 to 33 gauge (0.2 to 0.45 mm), and more preferably 30 to 33 gauge. Examples of a material for forming the needle tube 14 include stainless steel, aluminum, aluminum alloy, titanium, titanium alloy, other metals, and hard resins.

The tubular needle 14 is fixed to the needle hub 16 by the first member 22. The second member 24 is joined or fixed to the base end side of the first member 22. Examples of material for forming the first and second members 22 and 24 include resin materials such as polycarbonate, polypropylene, and polyethylene. Further, the needle hub 16 has an elastic member 26 inside the second member 24.

The first member 22 has a shaft part 28 that directly holds the tubular needle 14, the flange part 30 that extends radially outward from an outer peripheral surface of the shaft part 28 to form a flange, and an axially extending ring or annular projection 32 that protrudes axially toward the leading end from a leading end surface 30*a* of the flange part 30. The shaft part 28 is formed in a substantially columnar shape, and has a fixing hole 29 for accommodating and fixing the tubular needle 14 at the center axis. An adhesive 34 is injected into the fixing hole 29 with the tubular needle 14 inserted, whereby the tubular needle 14 and the first member 22 are fixed to each other.

The shaft part 28 has a storage portion 28*a* that is stored in the second member 24 and a protruding portion 28*b* that axially protrudes toward the leading end beyond the flange part 30. The protruding portion 28*b* of the shaft part 28 has a leading end surface 28*b*1 that slightly protrudes in the leading end direction beyond the leading end surface or forward-most surface of the ring or annular projection 32 and comes into contact with the surface of a living body. The tubular needle 14 fixed to the fixing hole 29 protrudes from the leading end surface 28*b*1 by an appropriate dimension (projection length). When the upper layer of the skin is to be punctured with the tubular needle 14, the leading end surface 28*b*1 contacts the surface of the skin to define a depth at which to puncture the skin with the tubular needle 14. That is, the depth of puncturing with the tubular needle 14 is determined by the protrusion length of the needle tube 14 with respect to the leading end surface 28*b*1.

The thickness of upper layer of the skin corresponds to the depth from the surface of the skin to the dermis layer, which is generally in the range of 0.5 mm to 3.0 mm. Therefore, the protrusion length of the tubular needle 14 with respect to the leading end surface 28*b*1 can be set in a range of 0.5 mm to 3.0 mm. More preferably, the protrusion length can be set in a range of 0.9 mm to 1.4 mm.

The size of the leading end surface 28b1 is set in consideration of the fact that the leading end surface 28b1 presses the skin around the tubular needle 14 to apply pressure to water bubbles formed on the upper layer of the skin. That is, the size of the leading end surface 28b1 is set so that the leading end surface 28b1 can press the skin around the tubular needle 14 to prevent the administered medicine from leaking. The distance from the peripheral edge of the leading end surface 28b1 to the peripheral surface of the tubular needle 14 can be in the range of 0.3 mm to 1.4 mm.

Figure 3:
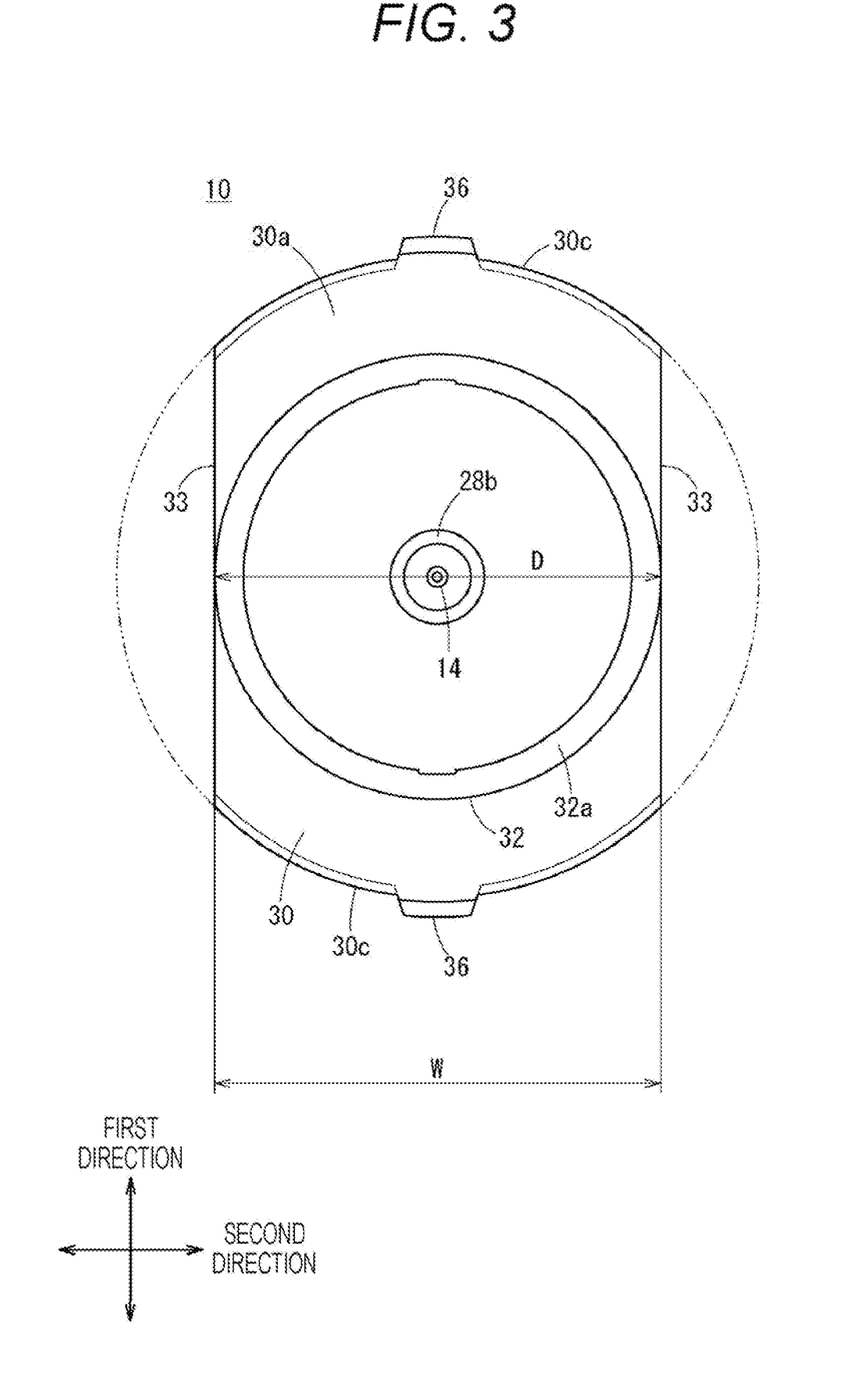
FIG. 3 is a front view of the intradermal needle shown FIG. 1 as viewed from a leading end side.

As shown in FIG. 3, the ring or annular projection 32 is a cylindrical wall-shaped portion that extends around or encircles a portion separated by a predetermined distance from the shaft part 28 (protruding portion 28b). The ring projection 32 protrudes a short distance toward the leading end side from the flange part 30. When the intradermal needle 10 is used, an end face 32a of the ring projection 32 entirely comes into contact with the skin of the living body. Thereby, the skin around the tubular needle 14 is strained, and the tubular needle 14 is maintained in a posture substantially perpendicular to the skin. As a result, it is possible to prevent shaking of the tubular needle 14 and make constant the puncture length of the tubular needle 14 with respect to the skin.

A diameter D of the ring or annular projection 32 is equal to or larger than the diameter of a water bubble formed on the skin. Specifically, the distance from the inner wall surface of the ring projection 32 to the outer peripheral surface of the protruding portion 28b is in a range of 4 to 15 mm. This makes it possible to prevent the ring projection 32 from applying the pressure to water bubbles and inhibiting the formation of water bubbles. When the diameter D of the ring projection 32 is increased, it is difficult to bring the entire end face 32a of the ring projection 32 into contact with the skin in a case of puncturing a narrow body part such as a child's arm with the tubular needle 14. Therefore, the distance from the inner wall surface of the ring projection 32 to the outer peripheral surface of the protruding portion 28b is preferably set to 15 mm or less.

As shown in FIG. 2, the flange part 30 is a part that extends in a disk shape radially outward from the shaft part 28. The flange part 30 is plate-shaped, extending from the outer peripheral surface of the shaft part 28 in a direction orthogonal to the center axis of the shaft part 28. The leading end surface 30a of the flange part 30 is a surface that comes into contact with the skin during use, and the leading end surface 30a is substantially parallel to the leading end portion of the ring projection 32. The diameter of the flange part 30 is in a range of 12 to 40 mm except for cut portions 33 described below.

In the present embodiment, the cut portions 33 are provided in the flange part 30 to enable use in a narrower body part. As shown in FIG. 3, a pair of cut portions 33 of the flange part 30 is provided. The two cut portions are positioned diametrically opposite one another, with the axis of the needle hub 16 interposed therebetween, and face away from one another. These cut portions 33 are formed in a shape in which a circular plate is cut by a pair of parallel straight lines extending in the first direction. As a result, the flange part 30 extends longer in the first direction and shorter in the second direction. The length (width W) of the flange part 30 as seen in the second direction is substantially the same as the diameter D of the ring projection 32. That is, the width W of the flange part 30 is reduced to a dimension substantially equal to the diameter D of the ring projection 32. This makes it easier to provide a safety mechanism such as a protector for preventing erroneous puncturing after use than in a case of forming the flange part 30 in a disk shape, and allows the use of the needle for a narrower body part.

The flange part 30 having the cut portions 33 is used such that the ring or annular projection 32 is pressed against the skin until an end portion 30c as seen in the first direction contacts the skin. With the cut portions 33, the flange part 30 is smaller in contact area with the skin than the conventional disk-shaped flange part.

In the conventional intradermal needle, the entire peripheral edge of the disk-shaped flange part is brought into contact with the skin, thereby assuring that the ring projection 32 and the tubular needle 14 can always apply a predetermined or more pressing force to the skin.

However, as a result of various studies performed by the inventors of the present invention, the inventors have discovered that the entire peripheral edge of the disk-shaped flange part does not need to be in contact with the skin. As a result of these studies, the inventors found that the ring projection 32 and the tubular needle 14 can always apply a predetermined or more pressing force to the skin when the peripheral edge of the flange part is contact with the skin at least at two places, preferably two diametrically opposed places with the needle hub 16 interposed therebetween.

Therefore, the flange part 30 of the present embodiment is provided with the pair of cut portions 33 as described above. Thus, the flange part 30 is downsized by the provision of the cut portions 33. In addition, the contact of the end portion 30c of the flange part 30 as seen in the first direction with the skin makes it possible to inform the user that the ring projection 32 is being pressed with an appropriate pressing force.

As shown in FIG. 2, an axial distance (height of the ring projection 32) on the axial direction of the needle hub 16 from the leading end surface 30a of the flange part 30 to the end face 32a of the ring projection 32 is set such that the skin can be punctured with an appropriate pressing force of the tubular needle 14 and the ring projection 32. The specific height of the ring projection 32 is determined according to the diameter D of the ring projection 32. The appropriate pressing force of the tubular needle 14 and the ring projection 32 is 0.5 N to 20 N, for example.

As shown in FIG. 1, a second member 24 is joined to a base end surface 30b that is a base end surface of the flange part 30 (a surface opposite to the leading end surface 30a provided with the ring projection 32). Further, a pair of claws 36 (see FIG. 3) is formed to protrude outward from an outer peripheral edge of the flange part 30 as seen in the first direction. The pair of claws 36 is provided at positions diametrically opposite to each other (positions differing by 180°) with the needle hub 16 interposed therebetween. These claws 36 are used to fix the intradermal needle 10 that is accommodated in a package 12 described later. In the illustrated embodiment, the claws lie in the plane of the flange part 30.

As shown in FIG. 2, the second member 24 is substantially cylindrically-shaped with a through hole 25 extending along the center axis. The storage portion 28a of the first member 22 is inserted into a leading end side of the through hole 25, while the elastic member 26 is accommodated in the middle of the through hole 25. At the time of assembly of an injection device 18, a nozzle inside a leading end portion 42 (see FIG. 5) of the syringe 20 is inserted into the base end side of the through hole 25. An inner peripheral surface on the base end side of the through hole 25 is formed in a tapered shape configured to make surface contact with an outer peripheral surface of the nozzle of the syringe 20.

A connection flange part 38 extending radially outward is provided at the leading end of the second member 24. A diameter of the connection flange part 38 is equal to or smaller than the width W of the flange part 30 of the first member 22 as seen in the second direction. A leading end surface 38a of the connection flange part 38 is fixed to the base end surface 30b of the flange part 30 by an appropriate fixing method such as vibration welding. A male screw portion 40 into which the leading end portion 42 of the syringe 20 is screwed is provided on the outer peripheral surface of the second member 24 on the base end side.

The elastic member 26 is a tubular connection or joint member that liquid-tightly holds the base end of the tubular needle 14 and causes the needle hole 15 to face the inside of the syringe 20. The elastic member 26 has a tubular needle hole part 48 provided inside. The tubular needle hole part 48 has an inner projection 50 for contacting and holding the inserted tubular needle 14. The elastic member 26 is fitted into the inner peripheral surface of the through hole 25 of the second member 24, and is firmly fixed or held by sandwiching an outer convex portion 52 projecting radially outward at the leading end side between the base end surface of the first member 22 and a step portion 24a of the second member 24.

Figure 4:
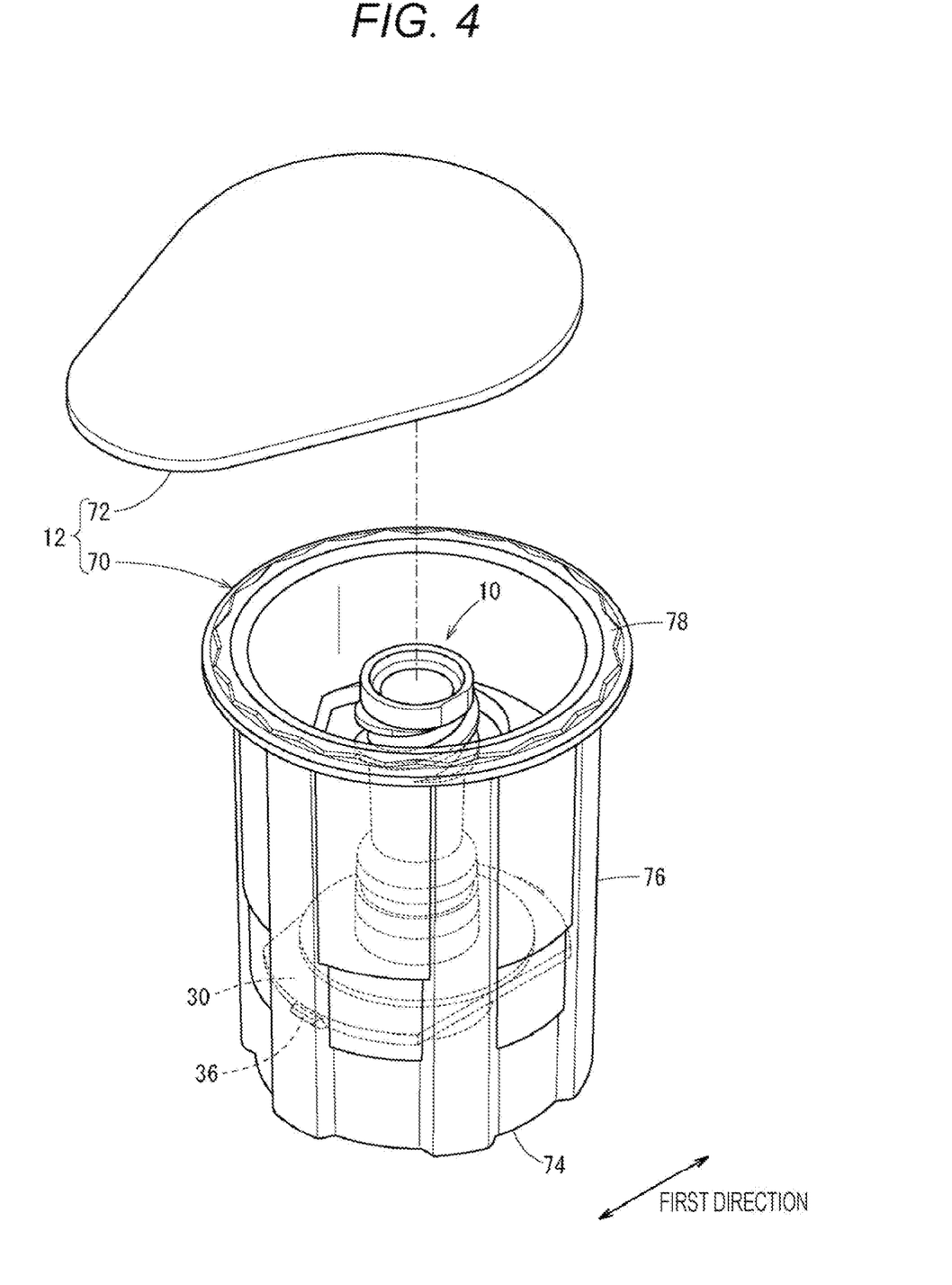
FIG. 4 is a perspective view of a package accommodating the intradermal needle shown FIG. 1.

The intradermal needle 10 according to the present embodiment is accommodated in a package 12 and provided as a product or article as shown in FIG. 4. Hereinafter, the package 12 accommodating the intradermal needle 10 according to the present embodiment will be described. The intradermal needle 10 is tightly enclosed in the package 12 and kept in a sterile state immediately before use.

The package 12 has a container 70 for accommodating the intradermal needle 10 and a seal member 72 for closing the container 70. The intradermal needle 10 can be removed from the container 70 by the user after peeling off the seal member 72 from the container 70 at the time of use.

The container 70 possesses a cylindrical shape having a space inside. The container 70 has a bottom surface 74 formed in a circular shape having a diameter slightly larger than the length of the flange part 30 of the intradermal needle 10 as seen in the first direction. The container 70 also has a cylindrical wall 76 that extends from the bottom surface 74 in the axial direction of the intradermal needle 10. The cylindrical wall 76 has an inner diameter slightly larger than the length of the flange part 30 of the intradermal needle 10 in the first direction. Further, the container 70 has a flange part 78 formed at an upper end. The seal member 72 is attached to the flange part 78.

Engagement portions (not shown) with which the claws 36 of the flange part 30 engage are provided at predetermined positions on the cylindrical wall 76 of the container 70. When the claws 36 engage with the engagement portions, the intradermal needle 10 is fixed inside the container 70 with a degree of strength or degree of hold that prevents the intradermal needle 10 from falling off. Further, the claws 36 prevent the intradermal needle 10 from rotating around when the syringe 20 is screwed into the intradermal needle 10.

Figure 5:
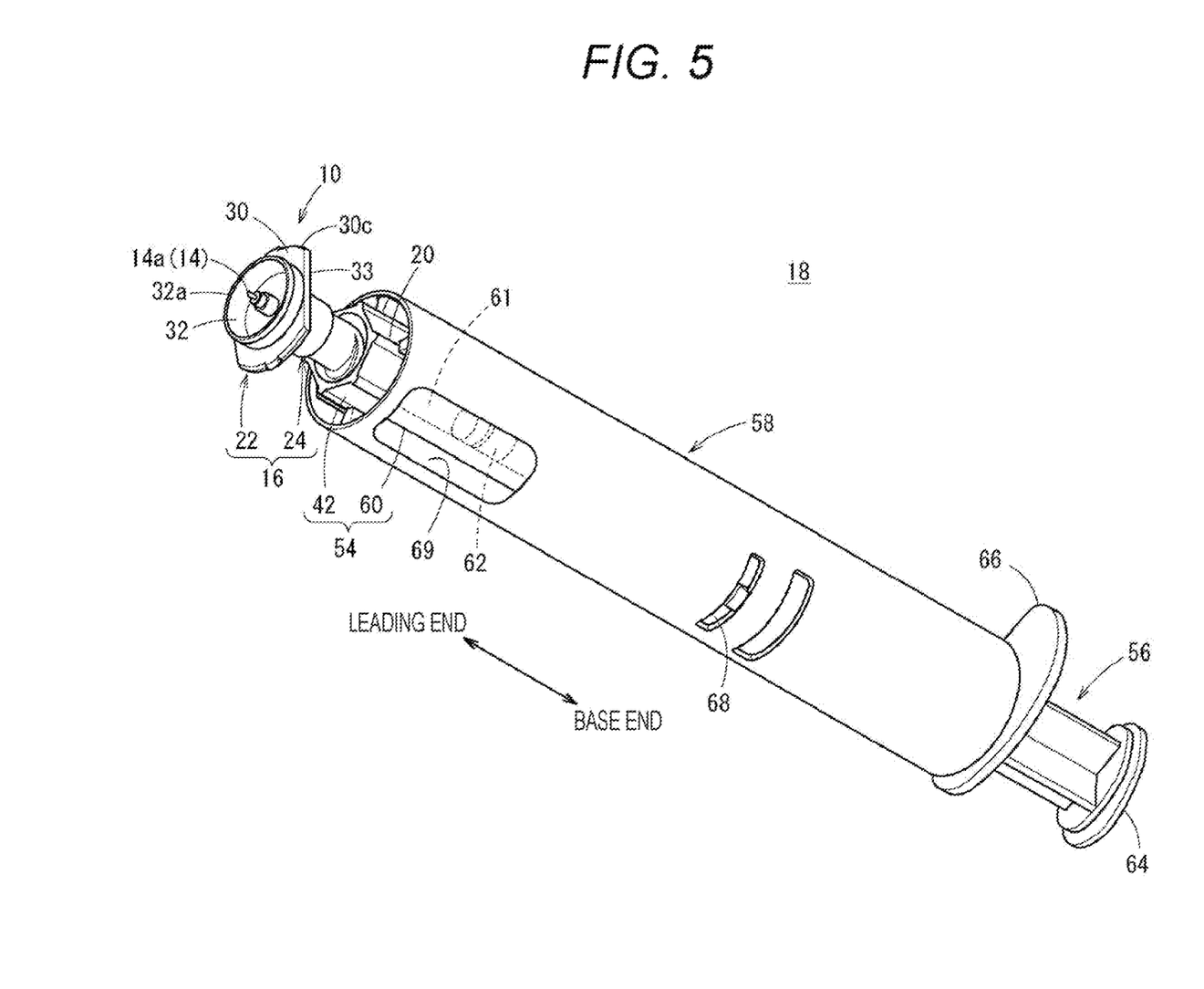
FIG. 5 is a perspective view of an injection device according to the embodiment.

The above-mentioned intradermal needle 10 is used by being assembled into the injection device 18 with the syringe 20 attached thereto as shown in FIG. 5. Hereinafter, the injection device 18 will be described. The syringe 20 is configured as a prefilled syringe filled with a drug solution in advance.

The syringe 20 has a female screw portion that is formed at the leading end portion 42 to engage with the male screw portion 40 of the intradermal needle 10. In addition, there is provided a nozzle communicating with a drug solution storage space 61 inside the leading end portion 42. In a state where the syringe 20 is attached to the male screw portion 40, a leading end surface of the leading end portion 42 contacts and presses the base end surface of the elastic member 26 (see FIG. 2).

The syringe 20 has a syringe main body 54, a plunger 56 that is inserted into or positioned in the syringe main body 54 in a state capable of relative axial movement, and a holder 58 that covers the outside of the syringe main body 54. The syringe main body 54 includes the above-described leading end portion 42, and a trunk part 60 that is connected to the leading end portion 42 and has the storage space 61 for storing a drug solution. On the other hand, the plunger 56 has at its leading end a gasket 62 that is liquid-tightly inserted into the storage space 61, and has at its base end an operating portion 64 for the user of the injection device 18 to perform a pressing operation. The syringe 20 may be of a type in which the gasket 62 is accommodated in the storage space 61 in advance and the plunger 56 is attached to the gasket 62 at the time of use.

The holder 58 is a cylindrical body that accommodates and fixes the syringe main body 54, and is provided to impart a larger diameter to the injection device 18 to facilitate the user's gripping operation. For this reason, a hook 66 is provided at a base end of the holder 58 for hooking on the user's finger when the operating portion 64 of the plunger 56 is pressed. The injection device 18 may not include the holder 58.

A plurality of support pieces (not shown) is provided on an inner wall forming an internal space of the holder 58 to support a leading end portion of the trunk part 60 of the syringe main body 54. Further, a locking window 68 is provided on an outer periphery of the holder 58 to lock a flange (not shown) at a base end of the syringe main body 54, and a viewing window 69 is provided near a leading end of the holder 58 to make visible the storage space 61 of the syringe main body 54.

The intradermal needle 10, the package 12 accommodating the intradermal needle 10, and the injection device 18 according to the present embodiment are basically configured as described above. Hereinafter, operations thereof will be described.

The intradermal needle 10 is provided in a state of being stored in the container 70 of the package 12 as shown in FIG. 4. As described above, in this state, the pair of claws 36 of the intradermal needle 10 is hooked on the engagement portions of the container 70, thereby preventing the intradermal needle 10 from falling off the package 12. Further, the package 12 encloses the intradermal needle 10 by attaching the seal member 72 to the flange part 78 of the container 70.

When the injection device 18 is used, the seal member 72 of the package 12 is peeled off, the leading end of the syringe 20 is inserted into the package 12, and the intradermal needle 10 and the leading end portion 42 of the syringe 20 are connected. That is, as shown in FIG. 5, the nozzle of the leading end portion 42 is inserted into the through hole 25 (see FIG. 2) of the second member 24, and the female screw portion of the leading end portion 42 is inserted into the male screw portion 40 of the intradermal needle 10 (see FIG. 2).

After completion of the connection between the intradermal needle 10 and the syringe 20, the syringe 20 is separated from the package 12. As a result, the pair of claws 36 of the intradermal needle 10 is disengaged from the engagement portions of the package 12, and the intradermal needle 10 and the syringe 20 in the integrated state are taken out of the package 12.

Thereafter, the tubular needle 14 of the intradermal needle 10 is inserted into the living body to inject the drug solution in the storage space 61 of the syringe 20. At that time, the user presses the ring or annular projection 32 and the tubular needle 14 of the intradermal needle 10 against the skin of the living body, and further pushes the ring projection 32 until the end portion 30c of the flange part 30 as seen in the first direction (see FIG. 1) comes into contact with the skin. At this time, the distance between the flange part 30 and the skin can be directly viewed through the cut portion 33. Thereby, the contact of the end portion 30c of the flange part 30 with the skin surface can be easily confirmed. As a result, the ring projection 32 and the tubular needle 14 are pressed against the skin with an appropriate pressing force, and the needle tip 14a of the tubular needle 14 is sent to an appropriate depth in the upper layer of the skin.

Even with the flange part 30 having the cut portions 33, the intradermal needle 10 as described above can inform the user of the same pressing force as that of the conventional intradermal needle having the disk-shaped flange part.

In addition, in the case of using the intradermal needle 10 for a narrow body part such as a child's arm, the intradermal needle 10 can push the ring projection 32 and the tubular needle 14 into the skin in a state where the cut portions 33 of the flange part 30 are oriented in a direction with space limitations. This facilitates the provision of a safety mechanism such as a protector to prevent erroneous puncturing after use, makes it easy to use the intradermal needle for a narrow body part, and allows the ring projection 32 and the tubular needle 14 to push into the skin by an appropriate pressing force with the contact of the end portion 30c of the flange part 30 as seen in the first direction as a guide.

Further, the distance between the end portion 30c of the flange part 30 and the skin can be visually checked from the cut portions 33 of the flange part 30 in a direct way. This makes it easy to check the appropriate amount of the intradermal needle 10 to be pushed so that the user can use the intradermal needle with security.

In addition, the intradermal needle 10 has the cut portions 33 on the sides of the flange part 30 having the largest outer diameter. This makes the intradermal needle 10 less likely to roll with improvement in ease of handling at the time of use.

EXAMPLES

Hereinafter, intradermal needles 10A to 10C according to examples of the embodiment will be described with reference to FIGS. 6A to 6C. In the intradermal needles 10A to 10C, the same features and components as those of the intradermal needle 10 described with reference to FIGS. 1 to 5 are denoted by the same reference numerals, and a detailed description of such components or features is not repeated.

Figure 6A:
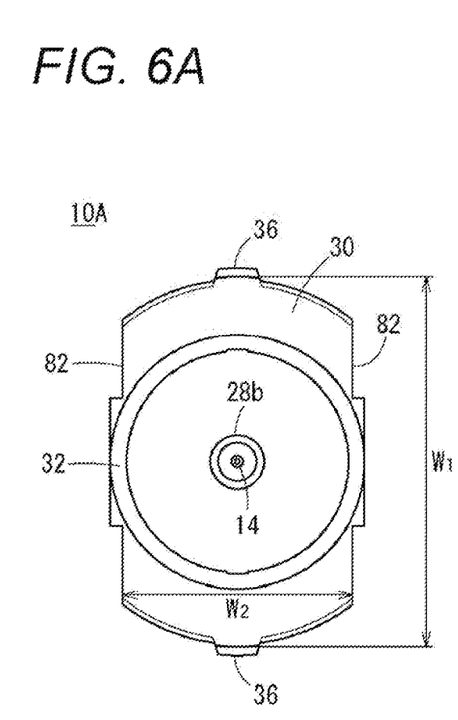
FIG. 6A is a front view of an intradermal needle according to a first example of the embodiment.

As shown in FIG. 6A, in the intradermal needle 10A according to a first example, a pair of cut portions 82 is formed on both side portions of the flange part 30. Since the cut portions 82 are formed in a step shape to avoid a ring projection 32, the cut portions 82 can be further reduced in area than a flange part 30. Thereby, in the intradermal needle 10A, since a width W2 of the flange part 30 can be made smaller than a diameter D of the ring projection 32. Thus, the intradermal needle 10A can be easily used for a narrower body part. As shown in FIG. 6A, the opposite ends of each cut portion 82 are connected to a curved portion of the outer peripheral of the flange part 30.

Figure 6B:
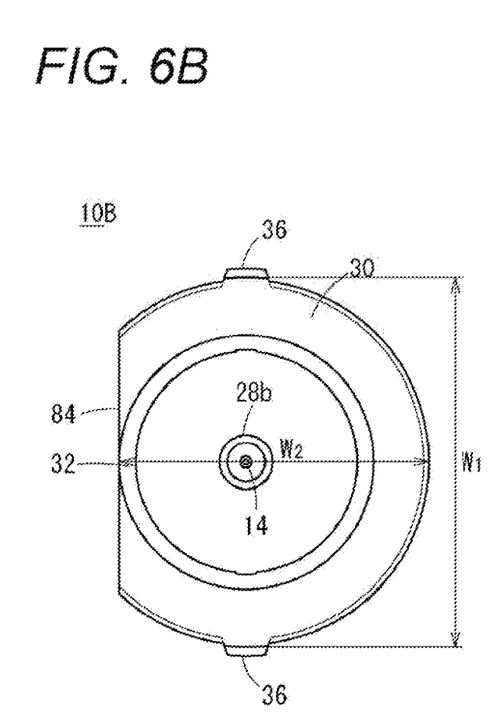
FIG. 6B is a front view of a intradermal needle according to second example of the embodiment.

As shown in FIG. 6B, in the intradermal needle 10B according to a second example, a cut portion 84 is formed only on one side of a flange part 30. Providing the cut portion 84 makes it possible to downsize the flange part 30, and inform the user of a pressing force equivalent to that of a conventional intradermal needle having a circular flange part. As shown in FIG. 6B, the opposite ends of the cut portion 84 are connected to a curved portion of the outer peripheral of the flange part 30.

Figure 6C:
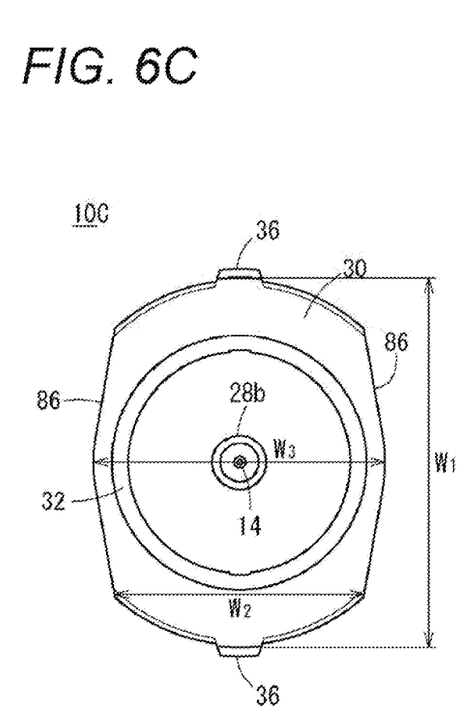
FIG. 6C is a front view of an intradermal needle according to a third example of the embodiment.

As shown in FIG. 6C, in the intradermal needle 10C according to a third example, bent cut portions 86 are provided on both sides of a flange part 30. As shown in the drawing, the cut portions 86 on each side are bent or angled, meaning the cut portion 86 on each side is comprised of two cut segments (straight portions) that are bent or angled relative to one another. As shown in FIG. 6A, the opposite ends of each cut portion 86 are connected to a curved portion of the outer peripheral of the flange part 30.

Figure 7:
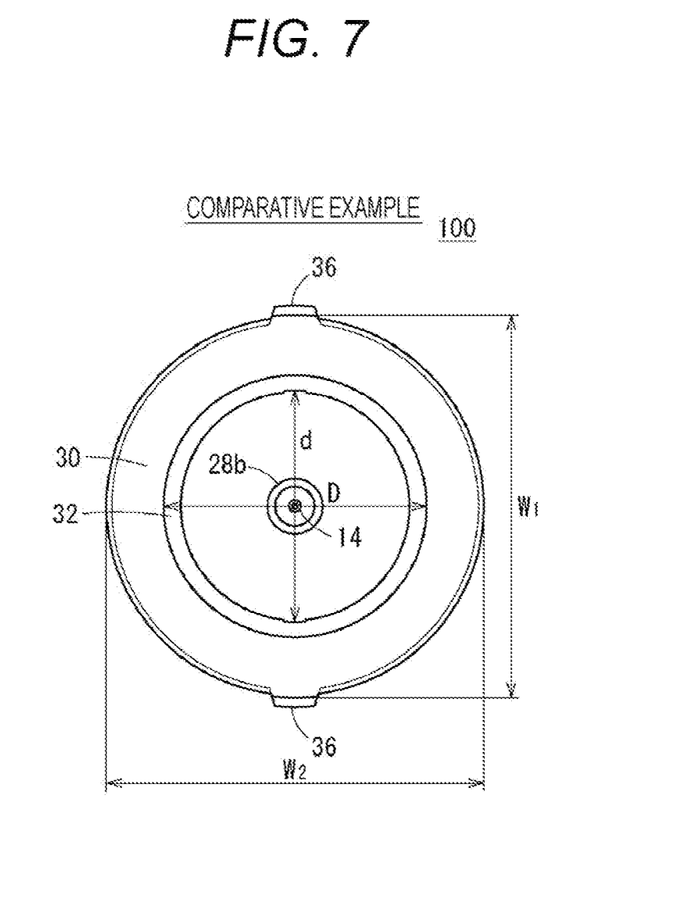
FIG. 7 is a front view of an intradermal needle according to a comparative example.
Figure 8:
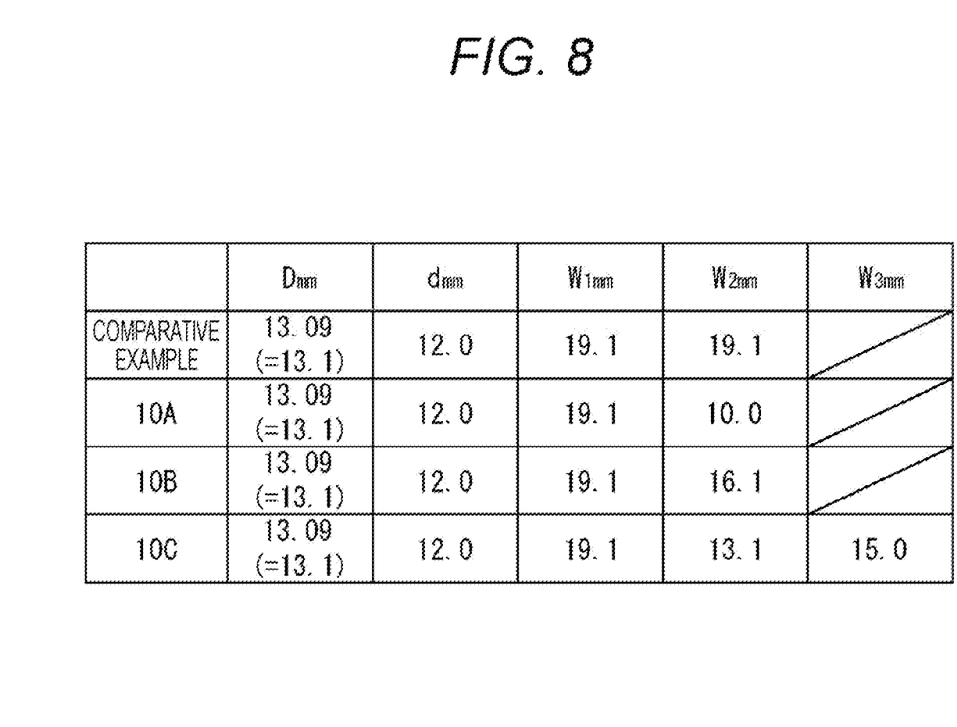
FIG. 8 is a table showing dimensions of flange parts of the intradermal needles according to the examples and the comparative example.
Figure 9A:
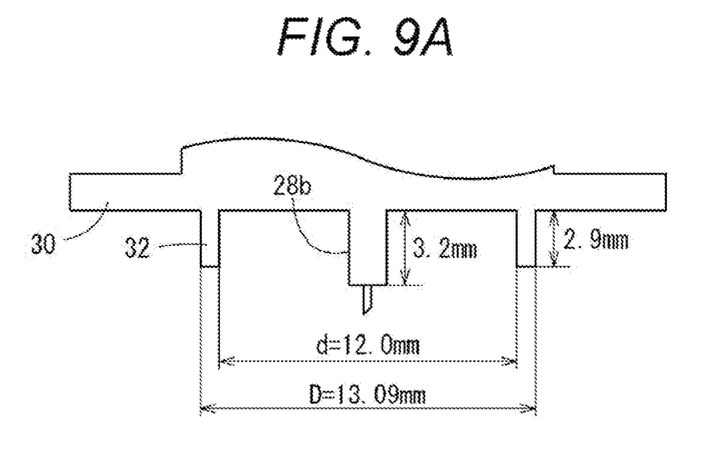
FIG. 9A is a cross-sectional view showing dimensions of ring projections and protruding parts of the intradermal needles according to the examples and the comparative example.
Figure 9B:
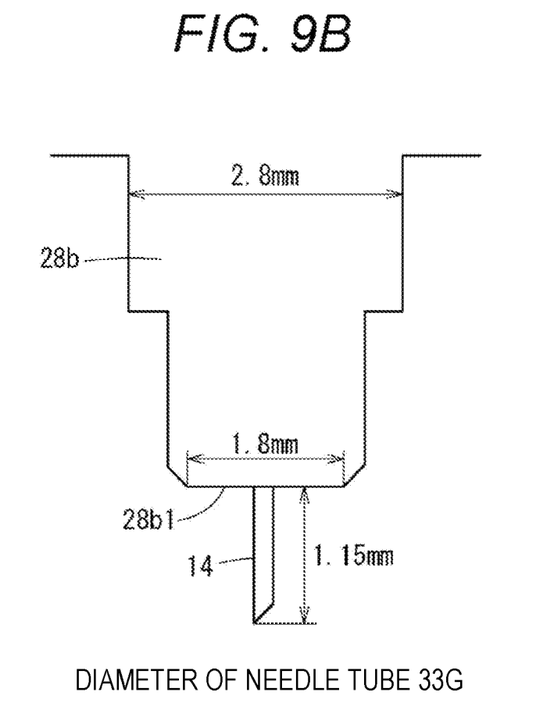
FIG. 9B is a cross-sectional view showing dimensions of protruding parts of the intradermal needles according to the examples and the comparative example.

The intradermal needles 10A to 10C according to the above examples and an intradermal needle 100 (FIG. 7) according to a comparative example were prototyped, and were evaluated in puncturing performance by comparison with a conventional intradermal needle. The intradermal needle 100 according to the comparative example shown in FIG. 7 has the flange part 30 formed in a circular shape. Further, dimensions W1, W2, and W3 of the respective portions of the flange parts 30 of the intradermal needles 10A, 10B, and 10C and of the intradermal needle 100 were set to values shown in the table of FIG. 8. The ring projection 32, protrusion portions 28b, and tubular needles 14 of the intradermal needles 10A, 10B, 10C, and 100 had the same shapes. FIGS. 9A and 9B show the dimensions of these components.

Next, the syringe 20 (see FIG. 5) was attached to each of the intradermal needles 10A, 10B, and 10C according to the examples and the intradermal needle 100 according to the comparative example. Then, these intradermal needles were subjected to a puncture test by which a silicone rubber sheet having a thickness of 15 mm and viscoelasticity equal to that of human skin was punctured with these needles. Here, taking into account variations in the force of the user, the puncture test was performed three times for each of the intradermal needles by 13 participants.

Thereafter, the punctured silicone rubber sheet was cut out, and the distance from the surface layer to the needle tip portion in the puncture mark of the silicone rubber sheet was measured using a caliper, and this measurement value was defined as the puncture depth. Then, a two-sample t test was performed on the puncture depths of the intradermal needles 10A, 10B, and 10C, with respect to the puncture depth of the intradermal needle 100 according to the comparative example.

As a result, it has been found that, in the case of each of the intradermal needles 10A, 10B, and 10C, no significant difference was observed in the puncture depth of the two specimens, and that the intradermal needles 10A, 10B, and 10C according to the examples were equivalent in puncturing performance to the conventional intradermal needle 100.

The detailed description above describes embodiments of an intradermal needle, a packaged article that includes an intradermal needle, and an injection device representing examples of the inventive intradermal needle, packaged article and injection device disclosed here. The invention is not limited, however, to the precise embodiments and variations described. Various changes, modifications and equivalents can be effected by one skilled in the art without departing from the spirit and scope of the invention as defined in the accompanying claims. For example, the syringe 20 may not be a prefilled syringe, but may be a syringe to be filled with a drug solution immediately before use. It is expressly intended that all such changes, modifications and equivalents which fall within the scope of the claims are embraced by the claims.

What is claimed is:

1. An intradermal needle comprising:
    a tubular needle that includes a needle tip configured to puncture a living body, the tubular needle possessing a central axis;
    a needle hub that holds the tubular needle in a fixed position so that the tubular needle and the needle hub are axially fixed relative to one another, the needle hub possessing a leading end configured to be brought into contact with a living body and a base end configured to receive a syringe;
    the needle hub comprising an elongated part and a flange part, the flange part being located at a leading end of the elongated part, the base end of the needle hub being an end of the elongated part that is opposite the leading end of the elongated part;
    the flange part extending radially outwardly from the elongated part, the flange part possessing a leading end side facing towards the leading end of the needle hub;
    an annular projection that extends axially away from the leading end side of the flange part toward the leading end of the needle hub, the annular projection possessing an outer periphery that is a continuous cylindrical shape, the annular projection surrounding a leading end portion of the tubular needle, the annular projection terminating in a free end constituting the leading end of the needle hub;
    the flange part including a cut portion along at least one portion of the flange part so that a width dimension of the flange part at the cut portion is less than the width dimension of the flange part at a part of the flange part other than the cut portion, the flange part including an outer periphery, the cut portion being a linearly extending portion of the outer periphery of the flange part, a part of the outer periphery of the annular projection being aligned with a part of the linearly extending portion of the outer periphery of the flange part so that the part of the outer periphery of the annular projection and the part of the linearly extending portion of the outer periphery of the flange part are flush with one another.

2. The intradermal needle according to claim 1, wherein the cut portion is provided in a region on an outer peripheral side of the annular projection.

3. The intradermal needle according to claim 2, wherein the cut portion includes a first cut portion in which one portion of the flange part is cut, and a second cut portion in which the flange part is cut at a position facing the first cut portion with the annular projection interposed therebetween.

4. The intradermal needle according to claim 3, wherein the first cut portion and the second cut portion are parallel to one another.

5. The intradermal needle according to claim 1, wherein the flange part is a disk-shaped flange part centered on an axis of the needle hub in a portion of the flange part other than the cut portion.

6. The intradermal needle according to claim 1, wherein the cut portion includes opposite ends each connected to a curved portion of the outer periphery of the flange part, the width dimension of the flange part at the cut portion being measured along a straight line passing through the central axis of the tubular needle and intersecting the cut portion, the width dimension of the flange part at the part other than the cut portion being measured along a straight line passing through the central axis of the tubular needle and intersecting the curved portions of the outer periphery of the flange part that are connected to the opposite ends of the cut portion.

7. The intradermal needle according to claim 1, wherein the outer periphery of the flange part in portions of the flange part other than the cut portion is curved.

8. The intradermal needle according to claim 1, wherein the cut portion of the flange part is a first cut portion, the flange part comprising a second cut portion positioned diametrically opposite the first cut portion, the outer periphery of the flange part in the first and second cut portions being linear while the outer periphery of the flange part in portions of the flange part other than the first and second cut portions are curved.

9. A packaged article comprising:
    a container possessing an open end;
    a seal member covering the open end of the container so that the container is a sealed container; and
    an intradermal needle positioned in the sealed container, the intradermal needle comprising:
        a tubular needle that includes a needle tip configured to puncture a living body;
        a needle hub that holds the tubular needle in a fixed position so that the tubular needle and the needle hub are axially fixed relative to one another, the needle hub possessing a leading end configured to be brought into contact with a living body and a base end configured to receive a syringe;
        the needle hub comprising an elongated part and a flange part, the flange part being located at a leading end of the elongated part, the base end of the needle hub being an end of the elongated part that is opposite the leading end of the elongated part;
        the flange part extending radially outwardly from the elongated part, the flange part possessing a leading end side facing towards the leading end of the needle hub;
        an annular projection that extends axially away from the leading end side of the flange part toward the leading end of the needle hub, the annular projection possessing an outer periphery that is a continuous cylindrical shape, the annular projection surrounding a leading end portion of the tubular needle, the annular projection terminating in a continuous circular free end constituting the leading end of the needle hub; and
        the flange part including a cut portion along at least one portion of the flange part so that a width dimension of the flange part at the cut portion is less than the width dimension of the flange part at a part of the flange part other than the cut portion, the flange part including an outer periphery, the cut portion being a linearly extending portion of the outer periphery of the flange part, a part of the outer periphery of the annular projection being aligned with a part of the linearly extending portion of the outer periphery of the flange part so that the part of the outer periphery of the annular projection and the part of the linearly extending portion of the outer periphery of the flange part are flush with one another.

10. The packaged article according to claim 9, wherein the flange part includes two claws that project outwardly from the outer periphery of the flange part and engage an interior of the container to inhibit the intradermal needle from rotating in the container when a syringe engages the intradermal needle when the intradermal needle is in the container.

11. The packaged article according to claim 10, wherein the flange part lies in a plane, the two claws lying in the plane and being positioned at diametrically opposite positions on the outer periphery of the flange part.

12. The packaged article according to claim 9, wherein the cut portion includes opposite ends each connected to a curved portion of the outer periphery of the flange part, the width dimension of the flange part at the cut portion being measured along a straight line passing through a central axis of the tubular needle and intersecting the cut portion, the width dimension of the flange part at the part other than the cut portion being measured along a straight line passing through the central axis of the tubular needle and intersecting the curved portions of the outer periphery of the flange part that are connected to the opposite ends of the cut portion.

13. The packaged article according to claim 9, wherein the outer periphery of the flange part in portions of the flange part other than the cut portion is curved.

14. The packaged article according to claim 9, wherein the cut portion of the flange part is a first cut portion, the flange part comprising a second cut portion positioned diametrically opposite the first cut portion, the outer periphery of the flange part in the first and second cut portions being linear while the outer periphery of the flange part in portions of the flange part other than the first and second cut portions are curved.

15. An injection device comprising:
an intradermal needle; and
a syringe detachably attached to the intradermal needle, the intradermal needle comprising:
a tubular needle that includes a needle tip configured to puncture a living body, the tubular needle possessing a central axis;
a needle hub that holds the tubular needle in a fixed position so that the tubular needle and the needle hub are axially fixed relative to one another, the needle hub possessing a leading end configured to be brought into contact with a living body and a base end configured to receive the syringe;
the needle hub comprising an elongated part and a flange part, the flange part being located at a leading end of the elongated part, the base end of the needle hub being an end of the elongated part that is opposite the leading end of the elongated part;
the flange part extending radially outwardly from the elongated part, the flange part possessing a leading end side facing towards the leading end of the needle hub; and
an annular projection that extends axially away from the leading end side of the flange part toward the leading end of the needle hub, the annular projection possessing an outer periphery that is a continuous cylindrical shape, the annular projection surrounding a leading end portion of the tubular needle, the annular projection terminating in a continuous circular free end constituting the leading end of the needle hub, and
the flange part including a cut portion along at least one portion of the flange part so that a width dimension of the flange part at the cut portion is less than the width dimension of the flange part at a part of the flange part other than the cut portion, the flange part including an outer periphery, the cut portion being a linearly extending portion of the outer periphery of the flange part, a part of the outer periphery of the annular projection being aligned with a part of the linearly extending portion of the outer periphery of the flange part so that the part of the outer periphery of the annular projection and the part of the linearly extending portion of the outer periphery of the flange part are flush with one another.

16. The injection device according to claim 15 wherein the cut portion includes opposite ends each connected to a curved portion of the outer periphery of the flange part, the width dimension of the flange part at the cut portion being measured along a straight line passing through the central axis of the tubular needle and intersecting the cut portion, the width dimension of the flange part at the part other than the cut portion being measured along a straight line passing through the central axis of the tubular needle and intersecting the curved portions of the outer periphery of the flange part that are connected to the opposite ends of the cut portion.

17. The injection device according to claim 15, wherein the outer periphery of the flange part in portions of the flange part other than the cut portion is curved.

18. The injection device according to claim 15, wherein the cut portion of the flange part is a first cut portion, the flange part comprising a second cut portion positioned diametrically opposite the first cut portion, the outer periphery of the flange part in the first and second cut portions being linear while the outer periphery of the flange part in portions of the flange part other than the first and second cut portions are curved.

19. An intradermal needle comprising:
a tubular needle that includes a needle tip configured to puncture a living body, the tubular needle possessing a central axis;
a needle hub that holds the tubular needle in a fixed position so that the tubular needle and the needle hub are axially fixed relative to one another, the needle hub possessing a leading end configured to be brought into contact with a living body and a base end configured to receive a syringe;
the needle hub comprising an elongated part and a flange part, the flange part being located at a leading end of the elongated part, the base end of the needle hub being an end of the elongated part that is opposite the leading end of the elongated part;
the flange part extending radially outwardly from the elongated part, the flange part possessing a leading end side facing towards the leading end of the needle hub;
an annular projection that extends axially away from the leading end side of the flange part toward the leading end of the needle hub, the annular projection possessing a continuous cylindrical shape and surrounding a leading end portion of the tubular needle, the annular projection terminating in a free end constituting the leading end of the needle hub; and
the flange part including an outer periphery, the outer periphery of the flange part including a first linearly extending portion defining a first cut portion and a second linearly extending portion defining a second cut portion, the first linearly extending portion and the second linearly extending portion intersecting one another at an intersection point and being oriented relative to one another at an angle other than 180°, the outer periphery of the flange part also including a curved portion forming part of a circle having a diameter, the first linearly extending portion and the second linearly extending portion being positioned entirely inside the circle.

20. An intradermal needle comprising:

a tubular needle that includes a needle tip configured to puncture a living body, the tubular needle possessing a central axis;

a needle hub that holds the tubular needle in a fixed position so that the tubular needle and the needle hub are axially fixed relative to one another, the needle hub possessing a leading end configured to be brought into contact with a living body and a base end configured to receive a syringe;

the needle hub comprising an elongated part and a flange part, the flange part being located at a leading end of the elongated part, the base end of the needle hub being an end of the elongated part that is opposite the leading end of the elongated part;

the flange part extending radially outwardly from the elongated part, the flange part possessing a leading end side facing towards the leading end of the needle hub;

an annular projection that extends axially away from the leading end side of the flange part toward the leading end of the needle hub, the annular projection possessing a continuous cylindrical shape and surrounding a leading end portion of the tubular needle, the annular projection terminating in a free end constituting the leading end of the needle hub;

the flange part including an outer periphery, the outer periphery of the flange part including a first linearly extending portion defining a first cut portion and a second linearly extending portion defining a second cut portion, the first linearly extending portion and the second linearly extending portion intersecting one another at an intersection point and being oriented relative to one another at an angle other than 180°;

the outer periphery of the flange part also including first and second curved portions that are spaced apart from one another by the first and second linearly extending portions so that the first and second linearly extending portions are positioned circumferentially between the first and second curved portions; and the flange part including: i) a first claw that protrudes outward away from the first curved portion; and ii) a second claw that protrudes outward away from the second curved portion.

* * * * *